(12) United States Patent
Zipper (10) Patent No.: US 11,471,179 B2
(45) Date of Patent: Oct. 18, 2022

(54) TISSUE FUSING CLAMP

(71) Applicant: Ralph Zipper, Melbourne, FL (US)

(72) Inventor: Ralph Zipper, Melbourne, FL (US)

( * ) Notice: Subject to any disclaimer, the term of this patent is extended or adjusted under 35 U.S.C. 154(b) by 992 days.

(21) Appl. No.: 16/081,943

(22) PCT Filed: Mar. 3, 2017

(86) PCT No.: PCT/US2017/020730
§ 371 (c)(1),
(2) Date: Sep. 3, 2018

(87) PCT Pub. No.: WO2017/152095
PCT Pub. Date: Sep. 8, 2017

(65) Prior Publication Data
US 2019/0090895 A1    Mar. 28, 2019

Related U.S. Application Data

(60) Provisional application No. 62/303,132, filed on Mar. 3, 2016.

(51) Int. Cl.
| | |
|---|---|
| *A61B 17/29* | (2006.01) |
| *A61N 7/02* | (2006.01) |
| *A61B 17/32* | (2006.01) |
| *A61B 18/14* | (2006.01) |
| *A61B 17/28* | (2006.01) |
| *A61B 18/00* | (2006.01) |

(52) U.S. Cl.
CPC .............. *A61B 17/29* (2013.01); *A61B 17/28* (2013.01); *A61B 17/320092* (2013.01); *A61B 18/1442* (2013.01); *A61N 7/02* (2013.01); *A61B 2017/320094* (2017.08); *A61B 2018/0063* (2013.01); *A61B 2018/00559* (2013.01); *A61B 2018/00619* (2013.01)

(58) Field of Classification Search
CPC . A61B 17/28; A61B 17/29; A61B 17/320092; A61B 18/08; A61B 18/082; A61B 18/1442; A61B 2017/320094; A61B 2018/00559; A61B 2018/00619; A61B 2018/0063; A61N 7/02
USPC .............................. 606/51–52, 169, 205–207
See application file for complete search history.

(56) References Cited

U.S. PATENT DOCUMENTS

| | | | |
|---|---|---|---|
| 2008/0105265 A1* | 5/2008 | Pannell | A61B 17/122 128/843 |
| 2013/0023875 A1* | 1/2013 | Harris | A61B 18/1445 606/47 |

* cited by examiner

*Primary Examiner* — Khadijeh A Vahdat (74) *Attorney, Agent, or Firm* — Lowndes; Stephen C. Thomas

(57) ABSTRACT

A tissue fusing clamp comprises a pair of components pivotably attached, having a component end with a finger loop for manipulation of the components, and each component having a fusing end comprising fusing jaws that are able to be motivated towards one another into a closed position. A depressor depresses tissue between the tissue areas to be fused, resulting in a tightening of the tissue after fusing. The fusing jaws may each comprise a fusing element, such as an ultrasonic transducer or laser, that is in electrical communication with a fusing circuit for providing electrical power to the fusing element as desired by a user. The fusing circuit may be controlled by use of a foot switch or other controller that may be manipulated by the user when it is desired to activate the fusing elements.

10 Claims, 12 Drawing Sheets

SECTION B-B
FORCEPS CLOSED (DEPRESSOR DOWN)

FORCEPS OPEN (DEPRESSOR UP)

FIG. 1a

FORCEPS CLOSED (DEPRESSOR DOWN)

FORCEPS OPEN - DEPRESSOR UP
(COVER PLATE AND THUMB SCREW NOT SHOWN)

FIG. 3

FORCEPS CLOSED - DEPRESSOR DOWN
(COVER PLATE AND THUMB SCREW HOT SHOWN)

FIG. 4

FORCEPS OPEN (DEPRESSOR UP)

FIG. 5

FORCEPS CLOSED (DEPRESSOR DOWN)

FIG. 6

SECTION A-A
FORCEPS OPEN (DEPRESSOR UP)

FIG. 7

SECTION B-B
FORCEPS CLOSED (DEPRESSOR DOWN)

FIG. 8

FORCEP OPENING DIAL VIEWS
ALL OTHER COMPONENTS HIDDEN FOR CLARITY

TOP VIEW - 20mm OPENING
FIG. 9

TOP VIEW - 6mm OPENING
FIG. 10

BOTTOM VIEW - 20mm OPENING
FIG. 11

BOTTOM VIEW - 6mm OPENING
FIG. 12

Forcep Option - Square
FIG. 13

Forcep Option - Dimpled
FIG. 14

Forcep Option - Smooth
FIG. 15

Forcep Tooth Option - With or Without
FIG. 16

1. ENSURE LOCKING KNOB IS LOOSENED (UNLOCKED).
2. TURN DIAL TO SELECT FORCEP OPENING WIDTH.
3. TIGHTEN LOCKING KNOB (ACTIVATES PLUNGER MOVEMENT).
4. AS FORCEPS ARE SQUEEZED TOGETHER, DEPRESSOR WILL MOVE TO APPROPRIATE DEPTH BASED ON PYTHAGOREAN'S FORMULA PRINCIPLE. (RED TRIANGLES ILLUSTRATE).

(DEPRESSED)  FIG. 21

TISSUE FUSING CLAMP

CROSS REFERENCE TO RELATED APPLICATIONS AND INCORPORATION BY REFERENCE

This international patent application claims the benefit of U.S. Provisional Application No. 62/303,132 titled TISSUE FUSING CLAMP which was filed in the United States Patent and Trademark Office on Mar. 3, 2016, which is hereby incorporated by reference in its entirety.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISK

Not applicable.

BACKGROUND OF THE INVENTION

1. Field of the Invention

The field of the invention relates generally to tissue fusing devices and methods that may be utilized in the fusing of human or non-human tissue, for example, during electrosurgery. More specifically, the invention relates to the repair of weakened, damaged or herniated human tissues, including but not limited to weakened vaginal tissue that results in conditions in women known as pelvic organ prolapse and urinary incontinence. Thus, in one embodiment, the field of the invention is also the field of methods and devices for fusing human vaginal tissue.

2. Background Art

Each year over 300,000 in the U.S. undergo surgery for pelvic organ prolapse. The majority are vaginal procedures. Between 17 and 30% of women will undergo a repeat surgery for recurrent pelvic organ prolapse. Over the last decade, in an attempt to improve on traditional suture repairs, synthetic meshes were marketed for the treatment of pelvic organ prolapse. By 2011 as many as on third of all vaginal prolapse surgeries were being performed with synthetic mesh. Although such synthetic patches had performed well in the treatment of abdominal hernias, such was not the case for the treatment of pelvic organ prolapse. Secondary to high complication rates associated with vaginal mesh implantation including severe and debilitating pelvic pain, severe pain with intercourse resulting in loss of consortium, up to a 20% incidence of mesh erosion into the vagina, and infection, the majority of manufacturers have ceased the marketing of synthetic mesh for the vaginal surgical repair of pelvic organ prolapse.

Although both individual surgical experts and large manufacturers continue to look for improved synthetic materials, the unique anatomy and physiology of the pelvis create an engineering dilemma that may preclude the creation of a synthetic material appropriate to the treatment of pelvic organ prolapse. The organs of the pelvis include the uterus, bladder, and bowel. The supporting structures of the vagina maintain the bladder, urethra, and rectum in positions that facilitate normal bladder function. Loss of such support results in bladder problems such as urinary incontinence, urinary retention, urgency of urination, frequency of urination, constipation, fecal incontinence and prolapse of the bladder, bowel, and vagina. Surgical correction of such by any method that does not allow for both support and normal levels of stretch and mobility can not only create new and worsening problems with bowel and bladder function, but can result in pelvic pain and an inability to have intercourse. Indeed, the non-elastic and contracting nature of plastic such as the polypropylene meshes previously marketed for the treatment of pelvic organ prolapse were a material mismatch that resulted in such severe complications. Any material implanted in the vagina will need to remain soft and elastic. Unfortunately, synthetic materials are recognized by the body as foreign and are attacked by the immune system. Even materials thought to be reasonably inert have been found to illicit a significant foreign body reaction. Hence, the endeavor to discover a device and or method to improve the treatment of pelvic organ prolapse is unlikely to result in the invention of a uniquely suited synthetic material.

The overwhelming majority of pelvic organ prolapse surgeries are once again being performed with suture. Weakened, damaged pelvic organ support tissues are being sewn together via methods that are over one hundred years old, colporrhaphies. Although complications associated with colporrhaphies are significantly lower and much easily treated than those associated with vaginal mesh, anatomic failure rates have been reported to be as high as 40-50% at one year. Secondary to the strong foreign body response associated with permanent suture, colporrhaphies are typically performed with absorbable suture. Once the suture dissolves, there is little left to hold together the weakened, damaged tissue. Prolapse returns.

What is needed in the art, and one of the objects of the present invention, is to provide a device and surgical method that allow the joining or fusion of supporting tissues in such a way that negates the need for both permanent sutures, absorbable sutures, clips, staples, synthetic meshes, or natural grafts. It is further the object of this invention to provide a device and surgical method that fosters the joining or fusion of tissues by stimulating the body's own repair mechanisms leading to the cellular proliferation and collagen remodeling, resulting in a repair that is void of any mismatched synthetic materials that could result chronic inflammation and loss of function. It is further the object of this invention to provide a method of suture-less colporrhaphy that is more durable than the presently performed suture colporrhaphies.

BRIEF SUMMARY OF THE INVENTION

The present invention comprises an apparatus and method for fusing human or non-human biological tissue that comprise one or more of the following features and/or steps, which alone or in any combination may comprise patentable subject matter.

One object of the invention is to provide an improved forceps or clamp and method that cause an imbrication of tissue. The appropriate performance of a vaginal colporrhaphy requires the pinching of tissue together in such a way that the tissue between the two points being sutured is inverted or pushed inward, away from the cavity of the vagina. This method, called imbrication, mobilizes vital structures such as the ureters, bowel, and nerves away from the tissue being pinched and decreases the risk of injury.

Another object of the invention is to provide an improved forceps or clamp and method that causes imbrication of tissue and allows the user to determine how much tissue will be imbricated.

Another object of the invention is to provide an improved forceps or clamp and method that both allows the joining or fusion of tissue with electrosurgery or ultrasound and imbricates tissue.

Another object of the invention is to provide an improved forceps or clamp for joining or fusing tissue with electorsurgery or ultrasound that monitors clamp pressure and the distance between the clamping ends of the forceps or clamp and provides such information to the generator.

Another object of the invention is to provide an improved forceps or clamp that increases the surface area of tissue joined or bonded.

In an embodiment, the tissue fusing claim of the invention comprises a first component and a second component pivotably attached to one another, wherein said first component comprises a first fusing jaw on a proximal end and wherein said second component comprises a second fusing jaw on proximal end, said fusing jaws for fusing tissue to be fused; a depressor attached to said components and disposed between said fusing jaws, said depressor adapted to be motivated in a direction away from said fusing jaws when said fusing jaws are motivated towards a closed position; wherein said motivation of said depressor causes said depressor to press against tissue located between the tissue to be fused, moving said tissue away from said fusing jaws; wherein said fusing jaws comprise fusing elements capable of fusing tissue.

In accordance with one embodiment of the present invention, the invention comprises a pair of components pivotably attached, having a component end with a finger loop for manipulation of the components, and each component having a fusing end comprising fusing jaws that are able to be motivated towards one another into a closed position. The fusing jaws may each comprise a fusing element that is in electrical communication with a fusing generator for providing electrical power to the fusing element as desired by a user. The fusing generator may be controlled by use of a foot switch or other controller that may be manipulated by the user when it is desired to activate the fusing elements. The movement of the fusion elements toward a closed position may cause movement of a depressor element in a direction perpendicular to the movement of the fusion jaws. This movement discourages excess tissue and intervening anatomy from being pinched between the closing fusion elements. The depressor element, which may be an elongated structure of any cross section, is mechanically linked to the components such that it is motivated away from the components as the components are motivated towards a closed position. The depressor element motivates a portion of tissue away from the fusing jaws while the fusing jaws grab tissue to be fused and pulls it into a fusing area located between the fusing jaws, increasing the area of tissue that is taken up by the fusing procedure.

The invention may be disposed in a closed position or an open position. The closed position may comprise an adjustable opening between the fusing jaws. The closed position is achieved by motivating the component finger loops towards one another until they come into contact with each other. The opening between the fusing jaws is adjustable in width by rotation of a dial which, when rotated, adjusts the opening between the fusing jaws to a desired distance that may be, for example, estimated by the user as the proper distance for grabbing a desired amount of tissue on either side of the depressor as the depressor is moving downward. Thus the dimension of the desired opening may be a function of the amount of tissue to be grasped between the fusing jaws of the components. The components may be manipulated into an open or closed position by the user.

When in the open position, no tissue is held between the fusing jaws. In this position the fusing circuit may be in a disarmed state which does not allow electric current to flow through the fusing elements located in the fusing jaws of the components. When in the closed position, tissue may be held between the fusing ends of the components, and the fusing elements may be activated by the user.

The face of each fusing jaw used for gripping and fusing tissue may comprise complimentary mechanical structures such as ridges or dimples which are offset and are complimentary when the fusing jaws are brought together. In the embodiment of the invention comprising ridges, the ridges may be of rectangular, semicircular or other cross section. This offset causes the surface area of tissue to be fused to be greater than if no offsetting complimentary structures are utilized. The offset structures, or protuberances, stretch the tissue to be fused as the fusing jaws are brought together, increasing the surface area to be fused and creating a stronger fusion than is achievable with the systems of the prior art. These offset protuberances have two effects: 1) they stretch the tissue to be fused and 2) they force tissue into tissue and allow for the transmission of energy in a horizontal direction into the spicules of tissue created by the protuberances.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating the preferred embodiments of the invention and are not to be construed as limiting the invention. In the drawings:

FIGS. 19 and 20 depict front and side views, respectively, of an embodiment of the tissue fusing clamp of the invention in a closed position in which the depressor is in a down position, showing the depressor plunge distance K and its relationship to the clamp opening width. As shown in FIG. 19, the plunge distance of this embodiment, K, is directly related to a value of approximately one half of the maximum clamp opening width, FW2.

DETAILED DESCRIPTION OF THE INVENTION

The following documentation provides a detailed description of the invention.

As used herein, "clamp" and "forceps" are used interchangeable and have the same meaning.

As used herein, "fusing element" means any device known in the medical arts for the fusing of human or non-human tissue, such as ultrasonic transducers or lasers.

As used herein, "tissue" includes all tissue including but not limited to human or non-human biologic tissue.

Although a detailed description as provided in the attachments contains many specifics for the purposes of illustration, anyone of ordinary skill in the art will appreciate that many variations and alterations to the following details are within the scope of the invention. Accordingly, the following preferred embodiments of the invention are set forth without any loss of generality to, and without imposing limitations upon, the claimed invention. Thus the scope of the invention should be determined by the appended claims and their legal equivalents, and not merely by the preferred examples or embodiments given.

Figure 1A:
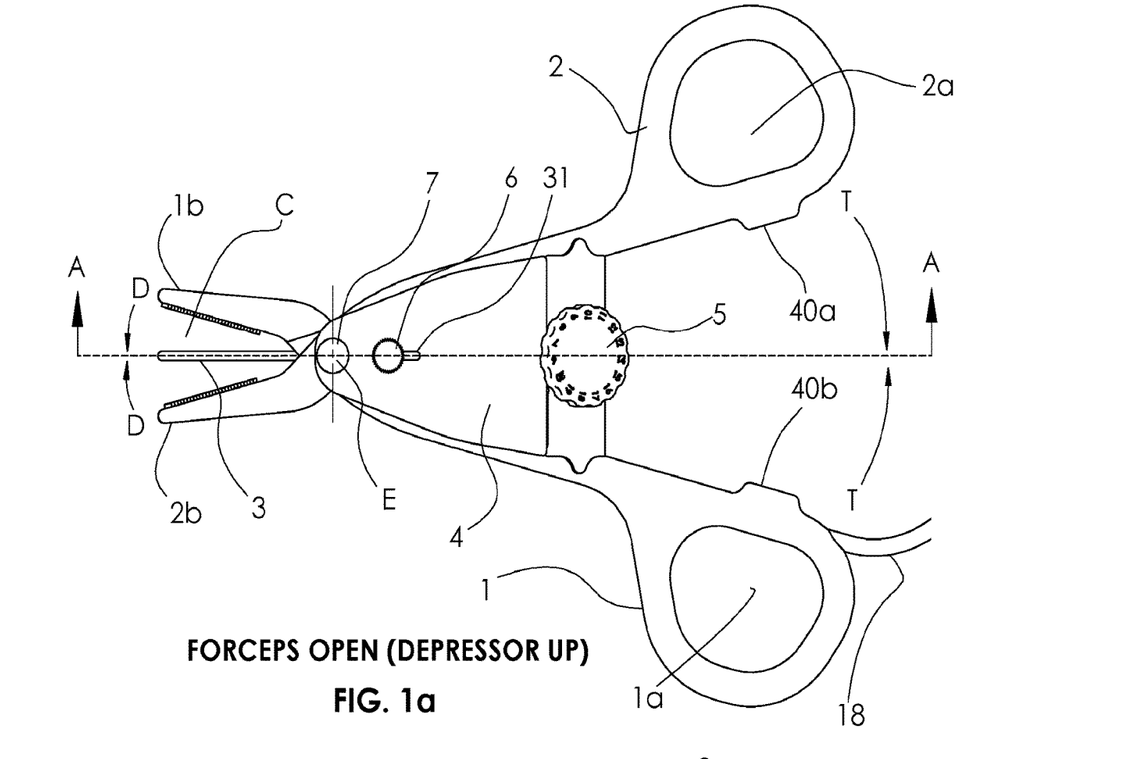
FIG. 1a depicts a top view of an embodiment of the tissue fusing clamp of the invention in an open position in which the depressor is in an up position.
Figure 1B:
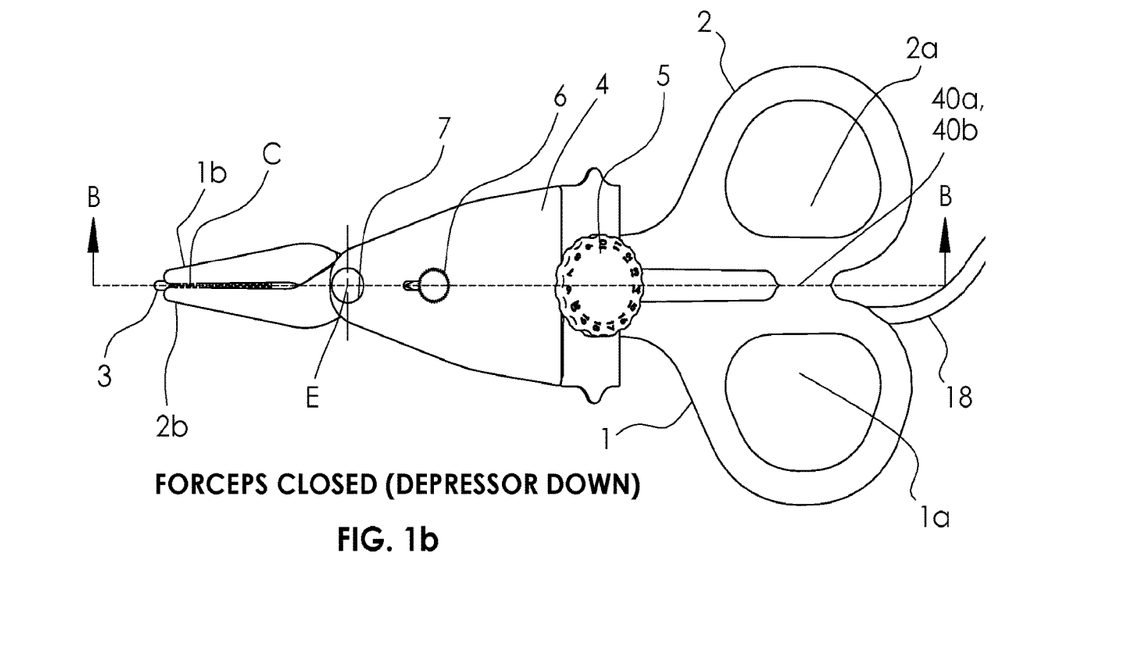
FIG. 1b depicts a top view of an embodiment of the tissue using clamp of the invention and a closed position in which the depressor is in the down position.

Referring now to FIGS. 1a and 1b, top views of an embodiment of the tissue using clamp of the invention are depicted, with the tissue fusing clamp shown in an open position in FIG. 1a and a closed position in FIG. 1b. A first component 1 having a finger loop 1a and a confusing jaw 1b is pivotably attached to a second component 2 having a finger loop 2a and a fusing jaw 2b. The pivotable attachment between first component 1 and second component 2 as provided by pin 7, which passes through both first component 1 and second component 2 and forms a pivoting engagement between them with axis of pivot E. When the user manipulates finger loops 2a and 1a together as shown by arrows T, the fusing jaws 1b and 2b are motivated together in the direction of arrows D, and the tissue of using clamp of the invention is disposed in a closed position as depicted in FIG. 1b. Thus, in FIG. 1a the tissue fusing clamp of the invention is shown in an open position and in FIG. 1b petition refusing clamp of the invention shown in a closed position. Thumbscrew 6, slot 31, depressor 3, cover 4 and dial 5 are all shown for reference. Cabling 18 comprises electrical conductors connecting the fusion generator with the fusing elements located in fusing jaws 1b and 2b. Typically, when in the closed position, protuberances 40a and 40b are in contact with one another, limiting further movement of the components toward one another as depicted in FIG. 1b. A male threaded stud of thumbscrew 6 may pass through slot 31 to be threadingly engaged in a matching female threaded hole 9a in wedge 9 (threaded hole 9a in wedge 9 are depicted in FIG. 2).

Figure 2:
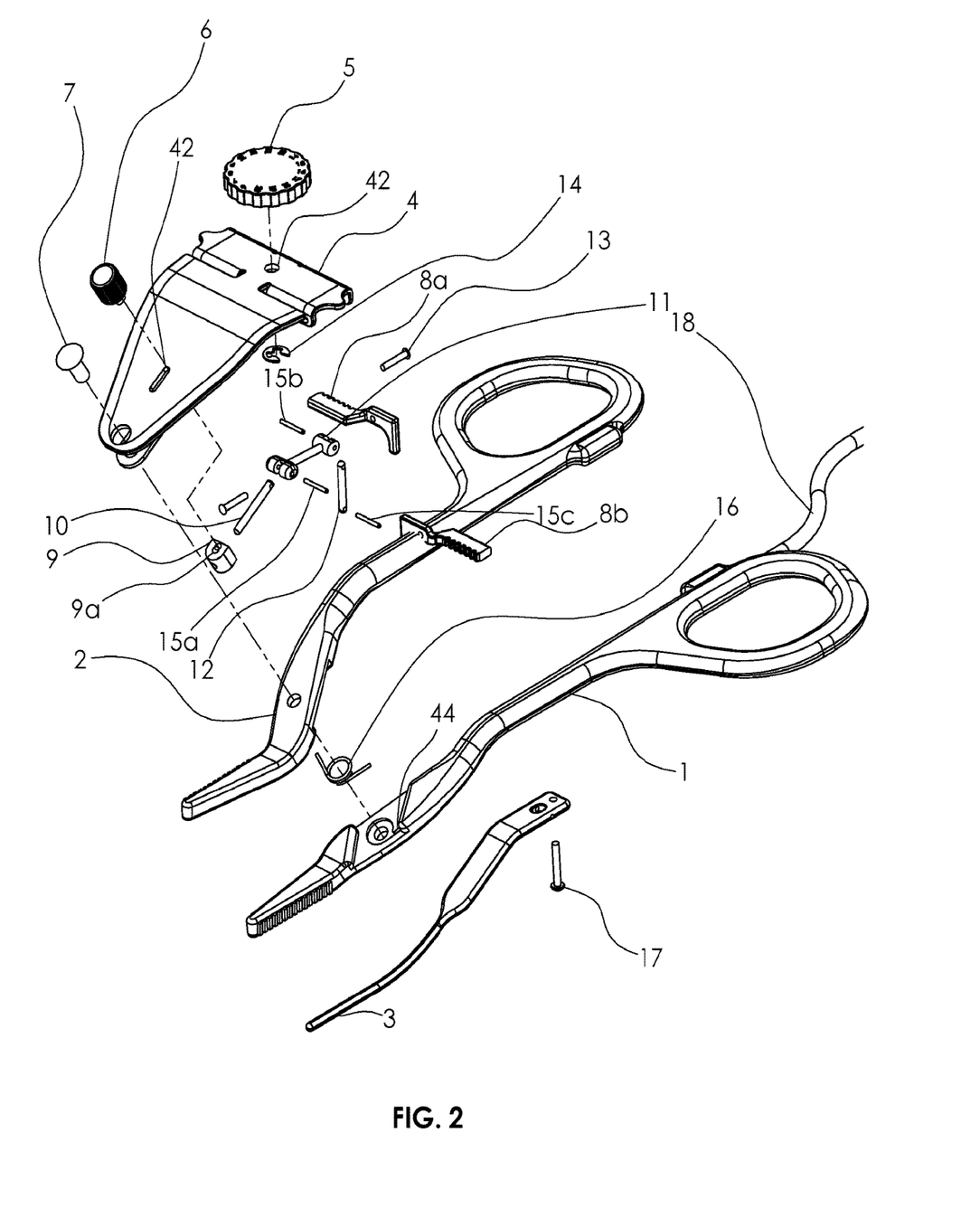
FIG. 2 depicts an exploded perspective view of an embodiment of the tissue fusing clamp of the invention.
Figure 3:
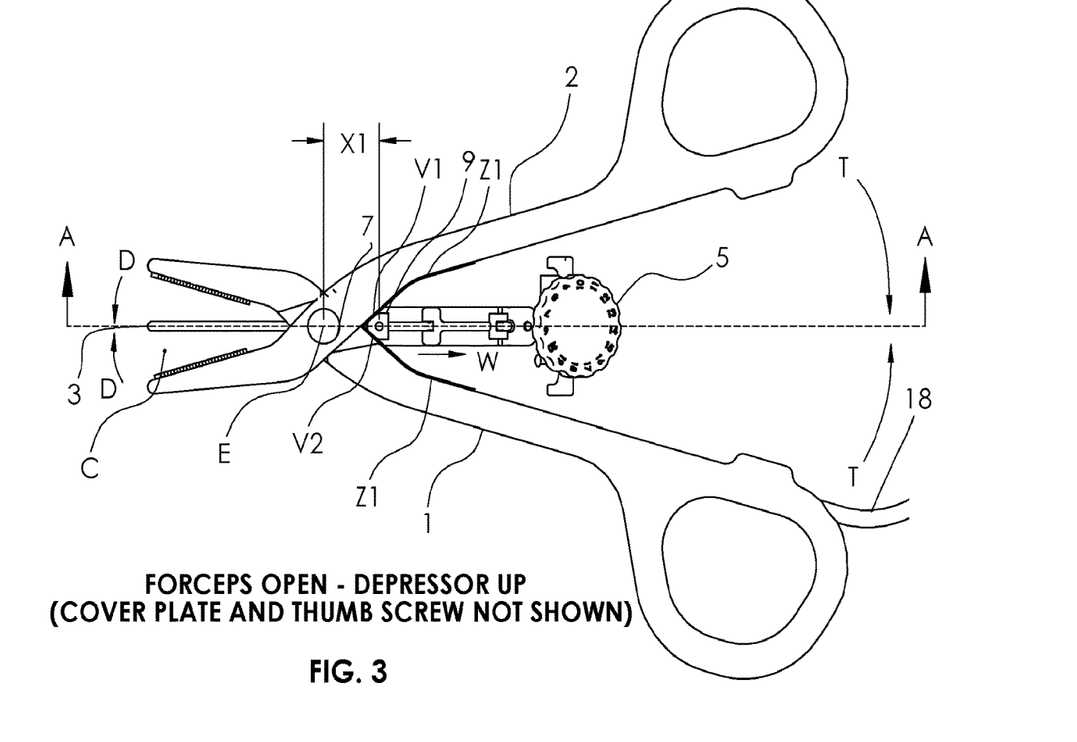
FIG. 3 depicts a top view of an embodiment of the tissue fusing clamp of the invention in an open position with the cover plate and thumbscrew removed for clarity.
Figure 4:
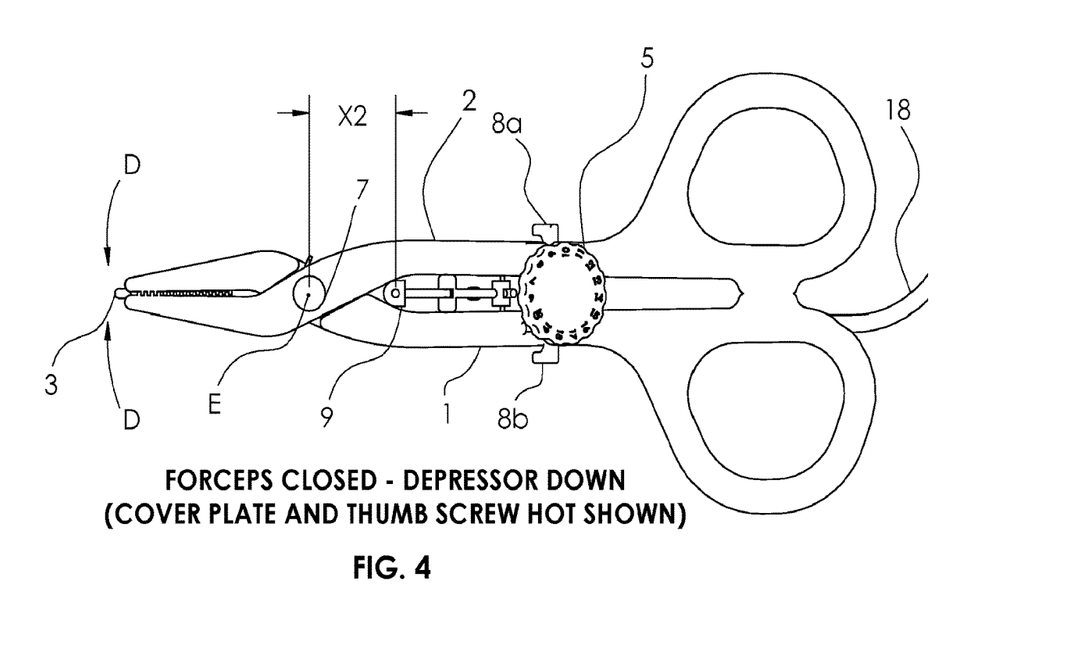
FIG. 4 depicts a top view of an embodiment of the tissue fusing clamp of the invention in a closed position with the cover plate and thumbscrew removed for clarity.
Figure 5:
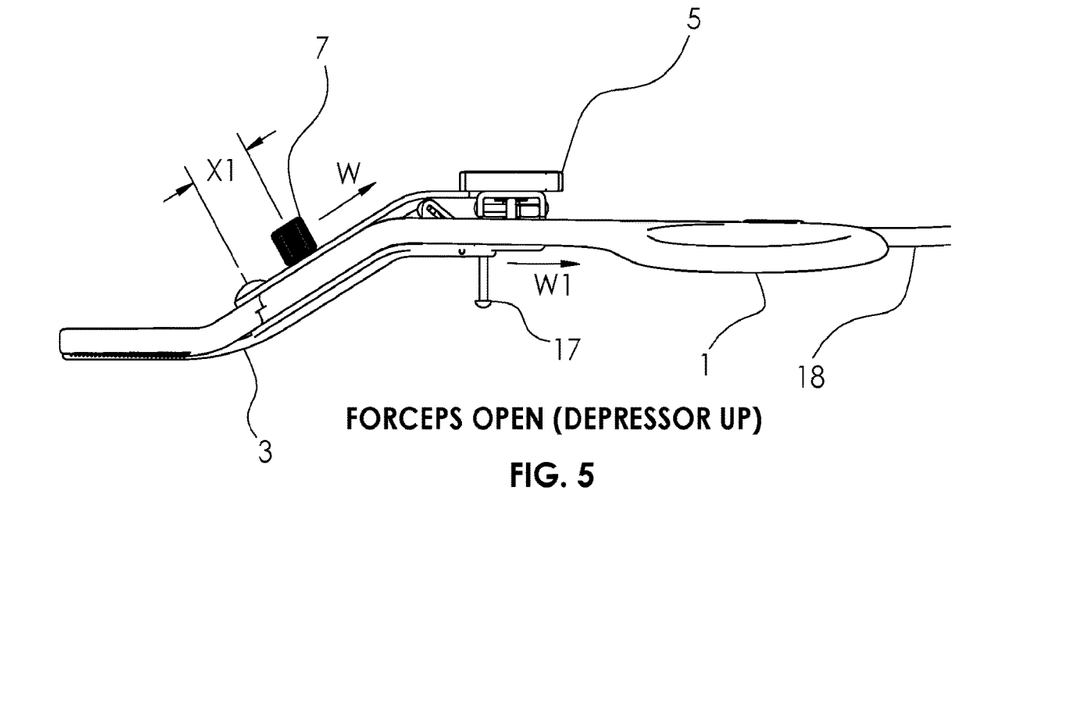
FIG. 5 depicts a side view of an embodiment of the tissue fusing clamp of the invention in an open position with the depressor in an up position.
Figure 6:
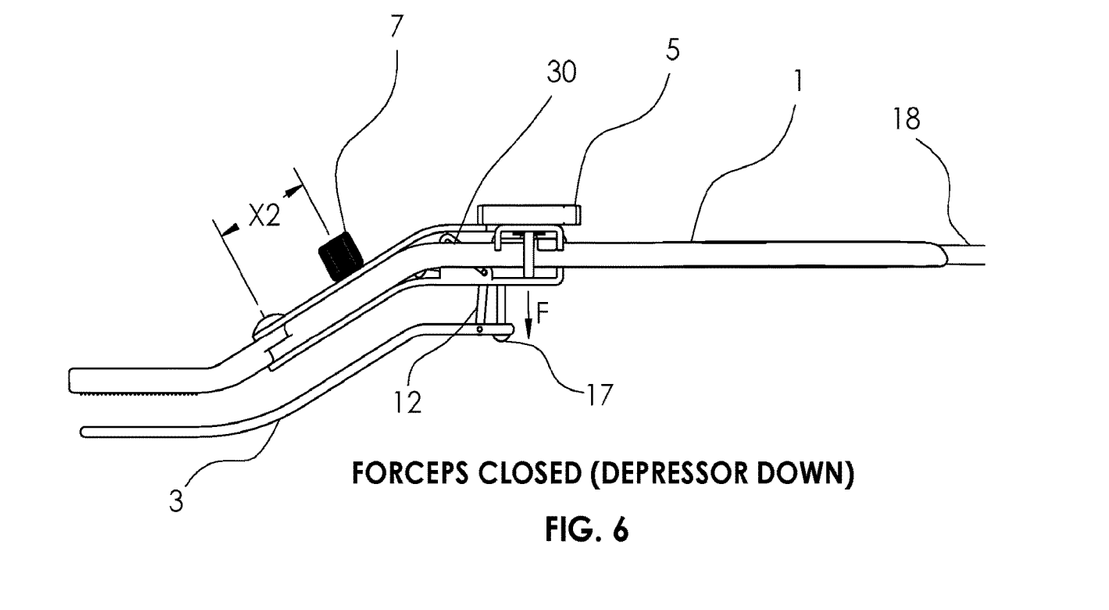
FIG. 6 depicts a side view of an embodiment of the tissue fusing clamp of the invention in a closed position with the depressor in a down position.

Referring now to FIG. 2, an exploded view of the tissue fusing clamp of the invention is depicted. Component 1 and component 2 are pivotably connected about pin 7 which also captures cover 4 to the components. Pin 7 provides the pivotable connection between component 1 and component 2. Spring 16 may reside in cutouts 40 and 41, and may be disposed about pin 7 such that pin 7 passes through a center opening of spring 16. Tangs of spring 16 may be in contact with surfaces of cutouts 40 and 41 such that a biasing force is imparted to the components, causing the components to be biased into the open position. Thus, the components may be biased into an open position and may remain in this position until the components are motivated together to dispose the tissue fusing clamp into a closed position. A male threaded stud of thumbscrew 6 may pass through slot 31 to be threadingly engaged in a matching female threaded hole 9a in wedge 9, and the threaded stud may bottom out on the outer surface of link 10 passing through hole 9b in wedge 9.

Figures 9, 10:
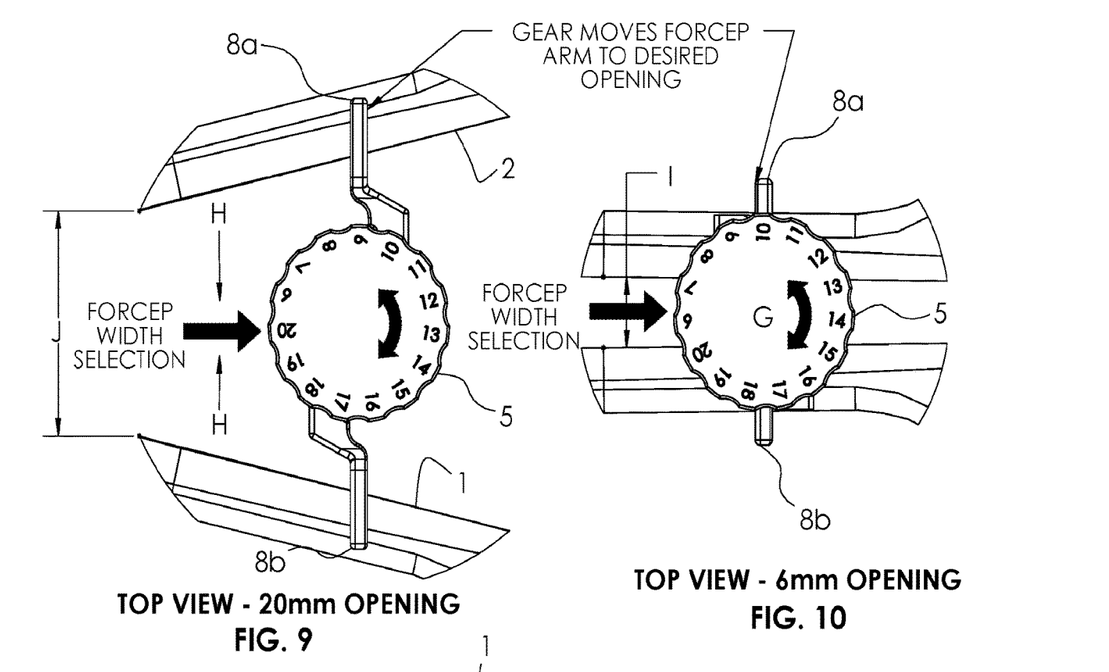
FIG. 9 depicts a top view of the width selecting dial of the invention, showing the movement of the components as related to the rotation of the dial. The clamp is set to a 20 mm opening.
FIG. 10 depicts a top view of the width selecting dial of the invention, showing the movement of the components as related to the rotation of the dial. The clamp is set to a 6 mm opening.
Figure 11:
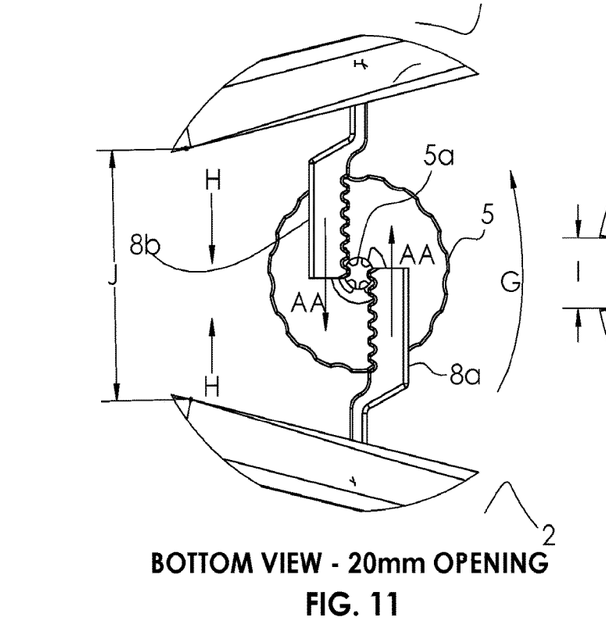
FIG. 11 depicts a bottom view of the width selecting dial of the invention, showing the movement of the components as related to the rotation of the dial. The clamp is set to a 20 mm opening.

Still referring to FIG. 2, dial 5 may comprise on its underneath side a post and gear 5a (5a is depicted in FIGS. 9 and 11). When dial 5 is assembled onto a top surface of cover for, the posted gear of dial 5 protrude through opening 42. The post on the underneath side of dial 5 may further comprise a slot for retaining lock ring 14 which may be snapped into place in a groove in the post on the underneath side of dial 5. In this manner, dial 5 may be retained in position on top of cover 4, with its post and gear protruding through opening 42 so as to be able to engage the teeth disposed in surfaces of first range limiter 8a and second range limiter 8b. This is further discussed in relation to FIGS. 9, 10, 11 and 12. Cabling 18 is shown for reference.

Downward Motivation of Depressor 3 when the Tissue Fusing Jaws are Closed

The links 10, 11, and 12 of the invention motivate depressor 3 downward when the components are motivated together. In an embodiment, the amount of downward movement K, or plunge, of depressor 3 can be adjusted by adjusting the fixation point of link 10 as it slides inside hole 9b in wedge 9, by tightening thumbscrew 6.

Referring now to FIGS. 2, 3, 4, 5, 6, 7 and 8, first link 10 may be fixed anywhere along its length to an internal surface of wedge 9 and may be pivotably connected to second link 11, said pivotable axis being formed by pin 15a passing through holes in a proximal end of second link 11 and a distal end of first link 10. Wedge 9 is fixable to link 10 at a desired location along the length of link 10 by sliding link 10 in hole 9b and tightening thumbscrew 6 into the threaded hole 9a in wedge 9.

In operation, a force is created by the closing of component 1 and component 2 into a closed position, the force acting upon wedge 9 and causing it to move rearward and upwards in the direction of arrow W as surfaces V1 and V2 (depicted in FIGS. 3 and 4) are in contact with and acting upon wedge 9. Thus, when component 1 and component 2 are motivated into a closed position, wedge 9 is moved in the direction of arrow W. When the components are disposed in an opened position, wedge 9 is separated from axis E by a minimum distance X1. However, when the components are motivated in the direction of arrows T to dispose the tissue fusing clamp in a closed position, the distance from axis E to wedge 9 is increased to X2. See FIGS. 3 and 4. X1 may be increased by fixation of the wedge 9 to link 10 at a position closer to link 11. This is facilitated by positioning wedge 9 closer to link 11 prior to fixation of wedge 9 by screw 6. The closer wedge 9 is affixed to link 11, the less is the excursion, or plunge, of depressor 3 in the direction F when the components are motivated into a closed position by a user, as described below.

Figure 7:
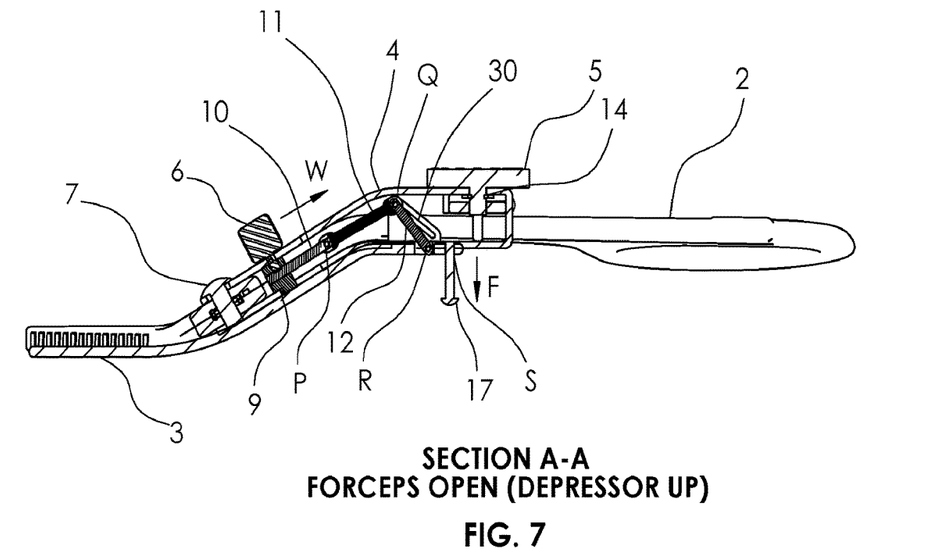
FIG. 7 depicts a cross-sectional view of a side view of an embodiment of the tissue using clamp of the invention in an open position in which the depressor is in an up position.
Figure 8:
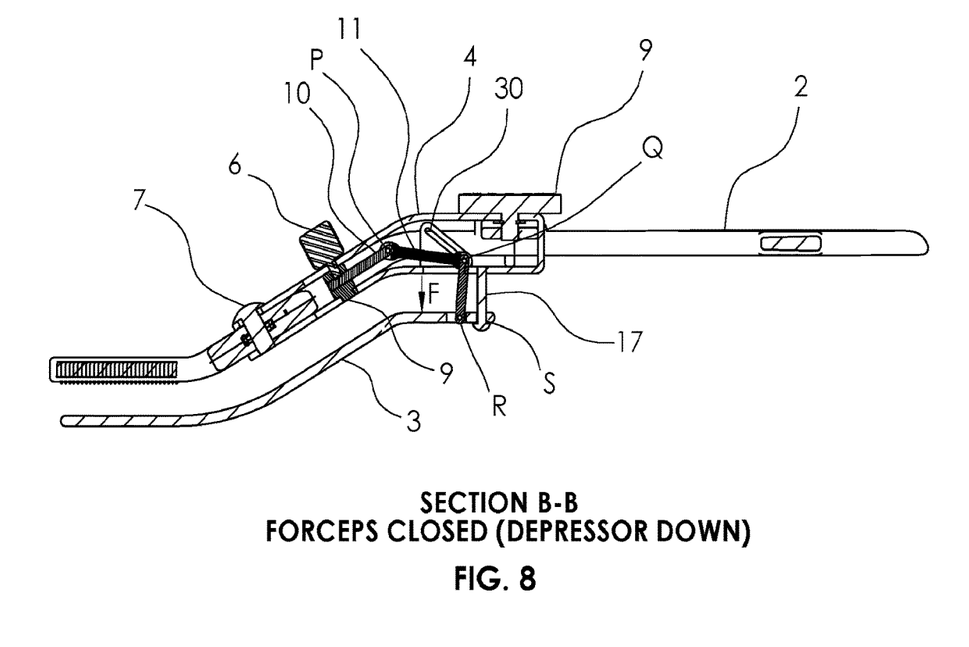
FIG. 8 depicts a cross-sectional view of a side view of an embodiment of the tissue using clamp of the invention in a closed position in which the depressor is in a down position.

Referring now to FIGS. 7 and 8, as wedge 9 is motivated in the direction W by the forces acting at points V1 and V2, link 10 is also motivated to move in the direction of arrow W because it is affixed to wedge 9 by the tightening of thumb screw 6. The distal end of link 10 is pivotably attached to a proximal end of link 11 at point P, and the distal end of link 11 is pivotably attached to a proximal end of link 12 at point Q. Furthermore, the distal end of link 11 and the proximal end of link 12 at point Q are constrained within slot 30 so that joint Q may only move along slot 30. Thus, when wedge 9 is motivated in the direction of arrow W by the forces applied at V1 and V2, link 10 acts to motivate point P in the same direction, with the result that point Q is motivated downward and backward along slot 30, pushing link 12 downward in the direction of arrow F. Because the proximal end of link 12 is attached to depressor 3, the downward motion of link 12 in the direction of arrow F causes depressor 2 to be motivated downward, with help from guide pin 17 for alignment. In this manner, a user may motivate component 1 and component 2 towards a closed position (i.e. towards one another in the direction of arrow T) and the linkages operate to motivate depressor 3 downward as the fusing jaws are closing together.

The Adjusting of Fusing Jaw Opening

Figure 12:
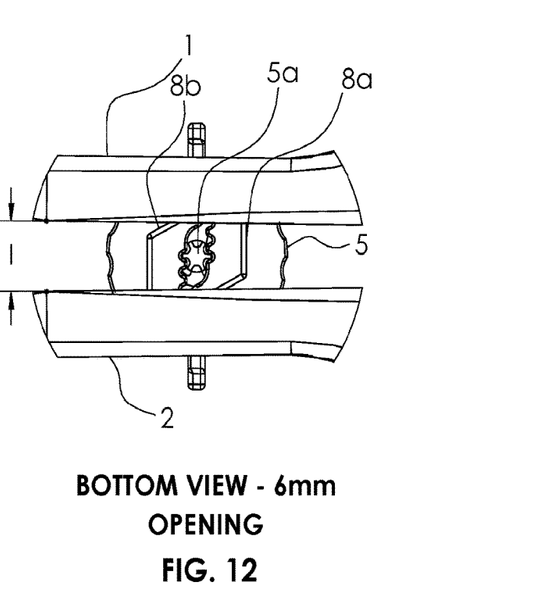
FIG. 12 depicts a bottom view of the width selecting dial of the invention, showing the movement of the components as related to the rotation of the dial. The clamp is set to a 6 mm opening.
Figures 17, 18:
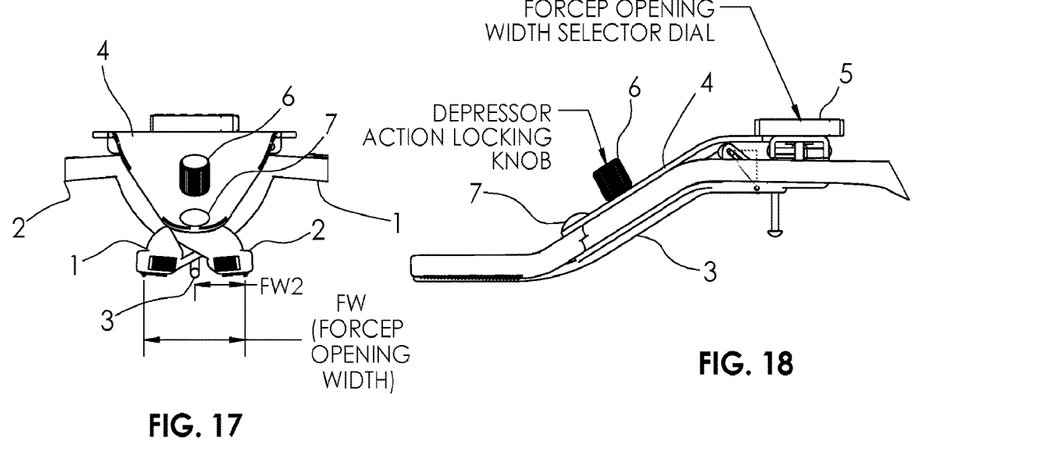
FIGS. 17 and 18 depict front and side views, respectively, of an embodiment of the tissue fusing clamp of the invention in an open position in which the depressor is in an up position. The maximum fusing jaw opening distance, set by the forceps width selector 5, is depicted as FW.

Dial 5 is used to adjust the limit of opening excursion of the fusing jaws. Referring now to FIGS. 9, 10, 11 and 12, a pair of clamp opening limiters 8a and 8b may be adjusted in the direction depicted as arrows H, and also adjusted opposite direction depicted as arrows H, by a user's rotation of dial 5. Gear 5a is disposed on an underneath side of dial five and comprises gear teeth that are engaged with matching teeth in surfaces of clamp opening limiters 8a and 8b. This is seen in FIGS. 11 and 12, which are bottom views of the engagement between the teeth of dial gear 5a with the teeth of clamp opening limiters 8a and 8b. As gear 5a is rotated in either direction as depicted by arrow G, gear opening limiters 8a and 8b are caused to move in the direction of arrow H or opposite the direction of arrow H. Each gear opening limiter comprises a mechanical tang, depicted as 8c and 8d in the figures, which operates to limit the excursion of components 1 and 2 in the direction opposite to direction T shown in FIG. 1a, and thus limiting the opening of the fusing jaws (depicted as forceps opening width in FIG. 17) to a desired opening dimension. In this manner a user may rotate dial 5 to a desired position that limits the opening of the fusing jaws, i.e. limits the dimension of forceps opening width, which may be twice the dimension of the depressor plunge distance K, to a desired opening dimension.

Figure 13:
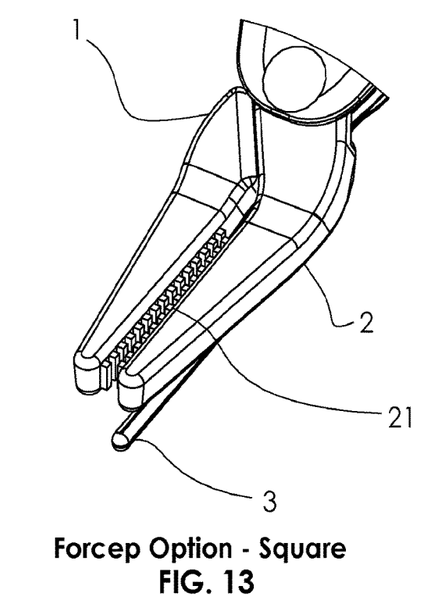
FIG. 13 depicts a perspective top view of an embodiment of the invention further depicting an embodiment of the fusing jaws of the invention in which the jaws comprise an alternating rectangular cross-section pattern on their tissue holding surfaces.
Figure 14:
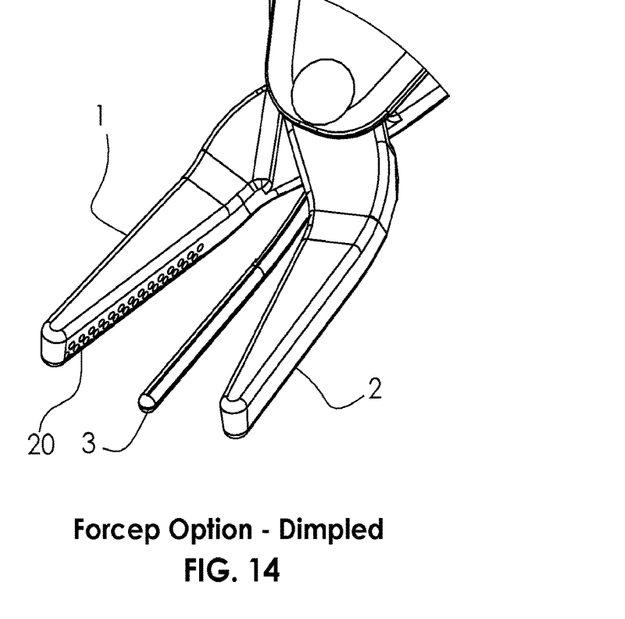
FIG. 14 depicts a perspective top view of an embodiment of the invention further depicting an embodiment of the fusing jaws of the invention in which the jaws comprise an alternating dimple cross-section pattern on their tissue holding surfaces.
Figure 15:
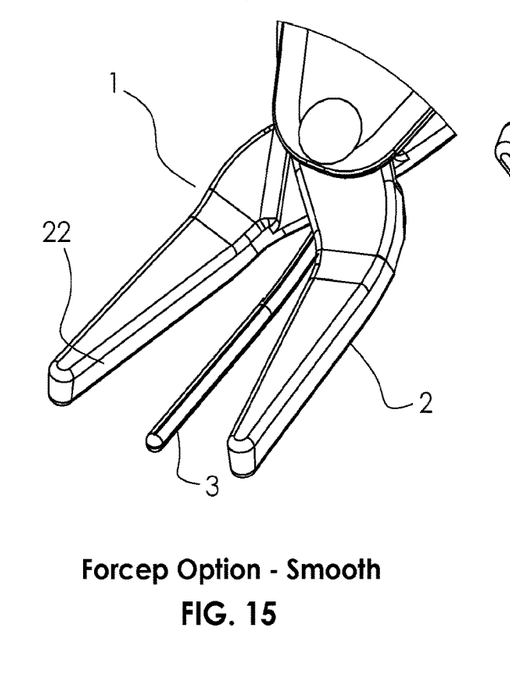
FIG. 15 depicts a perspective top view of an embodiment of the invention further depicting an embodiment of the fusing jaws of the invention in which the jaws comprise a smooth tissue holding surface.
Figure 16:
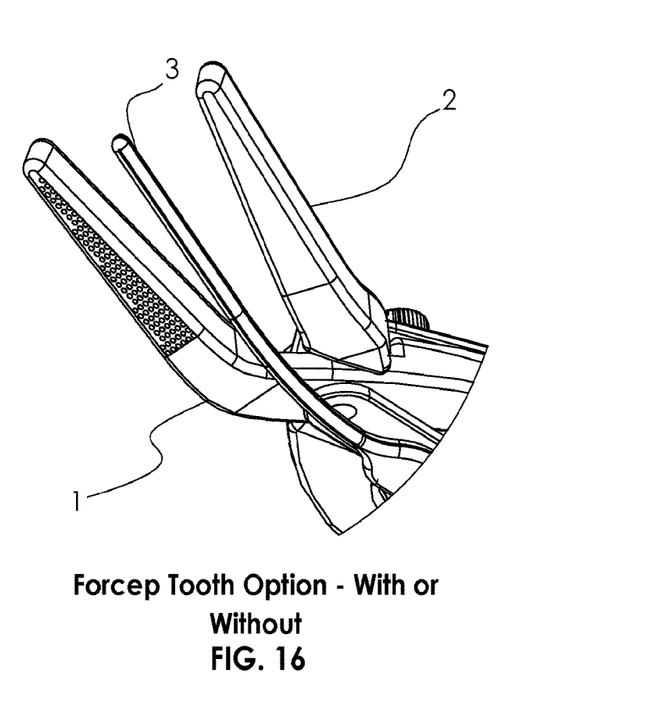
FIG. 16 depicts a perspective bottom view of an embodiment of the invention further depicting an embodiment of the fusing jaws of the invention in which either of the jaws may include an optional toothed or spiked cross section pattern for grabbing tissue on their underneath surfaces.

Referring now to FIGS. 13, 14, 15 and 16 various alternative embodiments for the tissue gripping surfaces of the fusing jaws are depicted. The fusion jaws of components 1 and 2, and depressor 3, are depicted in a top perspective view in FIGS. 13, 14 and 15, and in a bottom perspective view in FIG. 16. In a preferred embodiment, the features of the gripping surfaces of the fusing jaws are complementary features, which is to say that they are offset such that they nest together when diffusing jaws are brought into contact by causing the fusing jaw opening dimension, or forceps opening width, to be zero. The complementary nature of the tissue gripping surfaces of the fusing jaws operates to enhance the fusion of tissue by stretching the tissue between the complementary features, increasing the surface area for fusion and resulting in a more secure or fused area of tissue. Referring now to FIG. 13, the gripping surface of refusing jaws is shown to be a plurality of rectangular solid protrusions 21 in the surface of each fusing jaw. In this embodiment each rectangular solid protrusion 21 is offset from the rectangular solid protrusions in the opposing fusing jaw face, creating a complementary set of rectangular solid protrusions in the face of each fusing jaw such that the rectangular solid protrusions nest together, side by side rather than tip to tip, when the forceps opening width is brought to zero, causing the fusing jaws to come together. Referring now to FIG. 14, the offset complementary features 20 in each of the fusing jaw tissue clamping surfaces is depicted to be a plurality of raised dimples. In this embodiment each raised dimple 20 is offset from the raised dimples in the opposing using jaw face, creating a complementary set of raised dimples in the face of each fusing jaw such that the raised dimples nest together, side by side rather than tip to tip, when the forceps opening width is brought to zero, causing the fusing jaws to come together. Referring now to FIG. 15, an embodiment of the invention is depicted in which the tissue gripping face of each accusing jaw is shown to be a smooth surface. Referring now to FIG. 16, it is depicted that the underneath surface of each fusing jaw may further comprise a plurality of raised dimples, teeth or spikes or other surface features to aid in the gripping of tissue when the forceps are operated to grasp tissue, pulling the tissue up such that it is disposed between the fusing jaws in preparation for fusing the tissue.

The Relationship Between Fusing Jaw Opening and Depressor Plunge Distance K

Figures 19, 20:
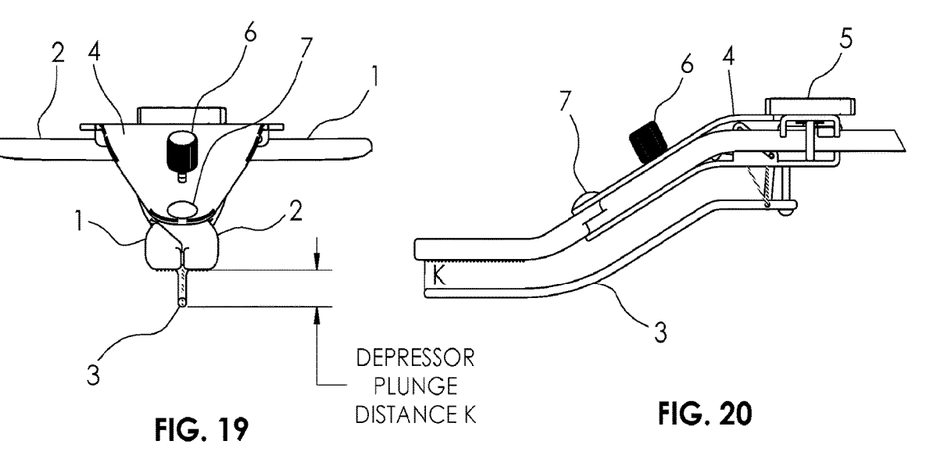
Figure 21:
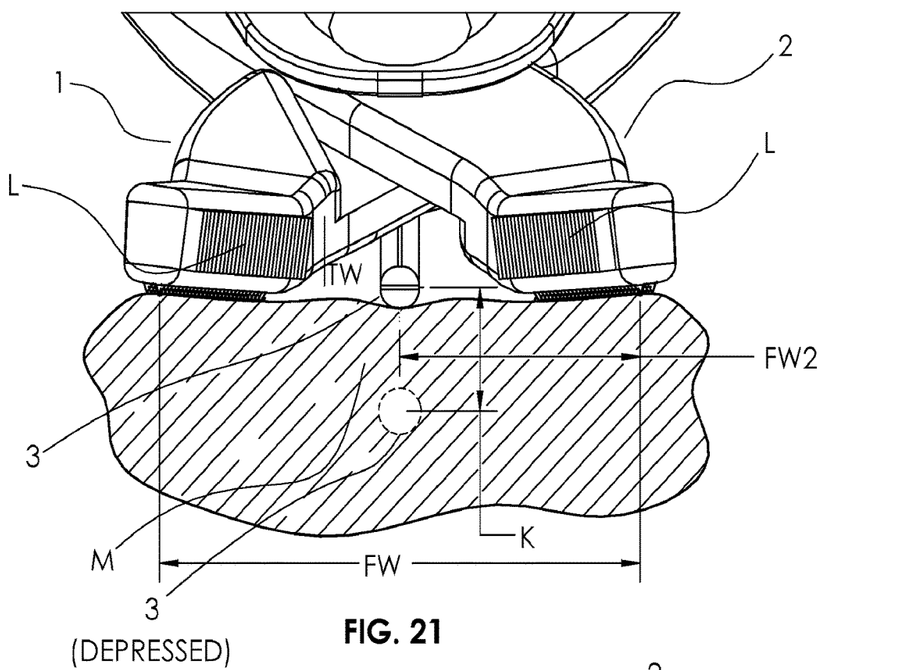
FIG. 21 depicts a front view of an embodiment of the tissue fusing clamp of the invention and an open position in which the depressor is in an up position, showing the depressor in contact with the tissue to be depressed and showing the fusing jaws of the invention in initial contact with the tissue to be fused, prior to the motivation of the fusing jaws into a closed position, which also motivates the depressor into a down position, and in which the fusing jaws have gripped the tissue to be fused and brought the tissue to be fused together at junction C.
Figure 22:
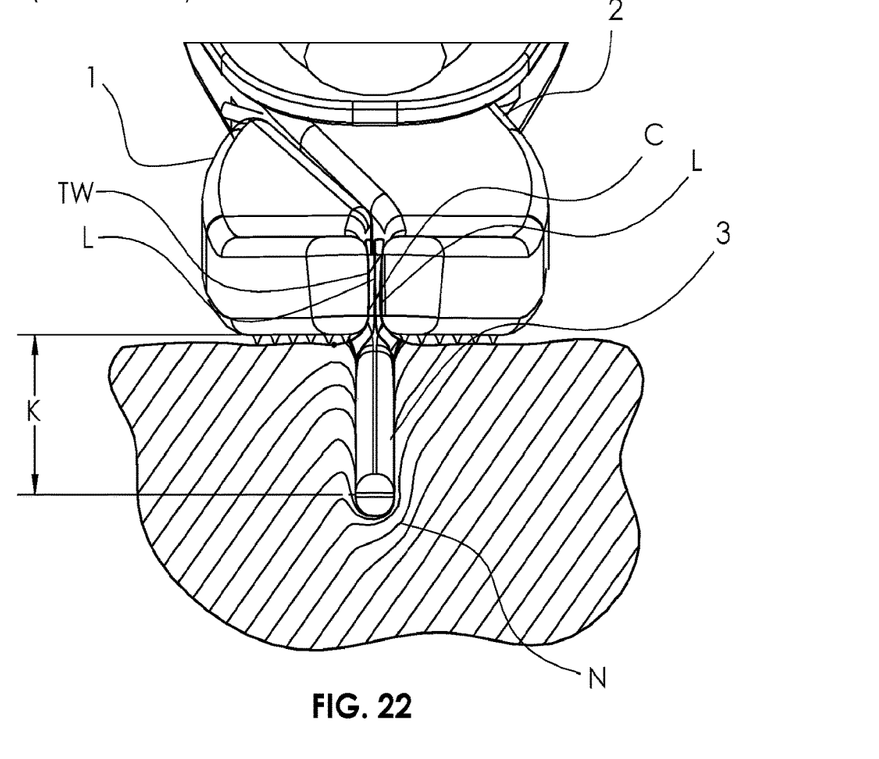
FIG. 22 depicts a front view of an embodiment of the tissue fusing clamp of the invention and a closed position in which the depressor is in a down position, showing the depressor depressing the tissue to be depressed and showing the fusing jaws of the invention gripping the tissue to be fused. This view occurs after the motivation of the fusing jaws into a closed position, which also motivates the depressor into a down position, and in which the fusing jaws have gripped the tissue to be fused and brought the tissue to be fused together at junction C.

Referring now to FIGS. 17, 18, 19, 20, 21 and 22, the dimensional relationship of a preferred embodiment, or best mode, of the invention is depicted. In a best mode, the forceps opening width is constrained to be a dimension substantially equivalent to twice dimension K, which is the depressor plunge distance. This relationship is preferred because the operation of depressor 3, pushing downward on tissue while the fusing jaws grasp tissue on either side of depressor 3 as they are brought together by operation of component 1 and component 2 as hereinbefore described, operates optimally to press down on tissue allowing tissue to be fused, located on either side of depressor 3 to be grasped at locations L by the fusion jaws and brought into a position where the tissue to be fused is optimally disposed between the fusing jaws so that it may be fused at tissue junction C as depicted in FIGS. 21 and 22. Depressor plunge depth K is determined by the lengths of links 10, 11 and 12 as is clearly seen in FIGS. 7 and 8. In a preferred embodiment and best mode, the length of each links 10, 11 and 12 are of such dimension that when a user operates component 1 and component 2 to motivate the tissue fusing clamp from the maximum forceps opening width to a closed position, with wedge 9 secured to link 10 for a maximum X2, the maximum forceps opening width is equal to twice depressor plunge depth K when depressor plunge depth K is measured as depicted in FIGS. 19 and 22. N is tissue that has been forced down by depressor 3.

Referring to FIG. 21, the height of the tissue to be fused, TW, is related to the ratio of K to FW2. When the ratio approximates one, TW will be minimal. Otherwise, the value of TW will be proportional to and approximate the difference between FW2 and K. Therefore the amount of tissue fused or welded between the fusion jaws may be directly controlled by adjusting the fixation position of the wedge 9 to the link member 10. In this best mode, the geometry of the inner surfaces of components 1 and 2 of FIG. 3, Z1, are shaped to cause an X2 that results in a K that is 1 mm to 10 mm less than FW2. However, in general, the shapes of surfaces Z1 may be any shape required to achieve a desired X2, and thus in the alternate embodiments X2 may take any desired value.

While the best mode of the invention is the embodiment in which the fusing jaws opening width (also referred to as forceps opening width) is 0 mm to 10 mm greater than twice depressor plunge distance K, any other dimensional relationship between the fusing jaws opening with any depressor plunge distance K are within the scope of the invention. For example, it may be determined by experimentation that certain relationships between fusing jaws opening width a depressor plunge distance of K may be optimal in certain tissue fusing applications, for particular body or tissue types, patient ages, or in other circumstances. Thus the scope of the appended claims is not to be construed as necessarily being limited to the specific relationship set forth above in the description of the best mode of the invention.

Figure 23:
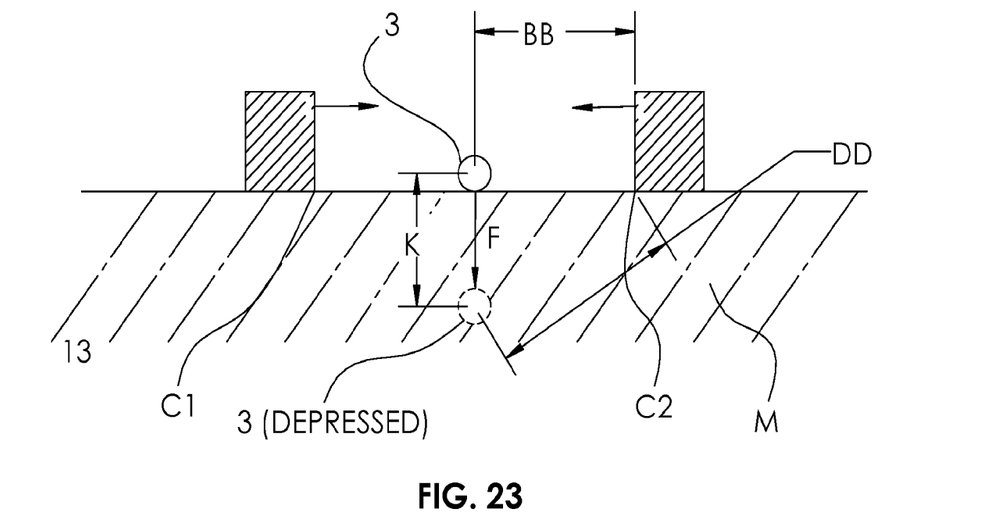
FIG. 23 depicts a view of the fusing jaws in an open position, with tissue to be fused about to be disposed between the fusing jaws.

Referring now to FIG. 23, a view of the fusing jaws in an open position, with tissue to be fused about to be disposed between the fusing jaws, is depicted. Tissue is depicted as M. In FIG. 23, the fusing jaws have not yet begun to be motivated together towards a closed position. The area of tissue that will be "taken up" in the fusing procedure is the tissue between points C1 and C2. This tissue, less the difference between BB and CC, a difference created by the fixation point of wedge 9 to link 10, will be motivated downward in the direction of arrow F. Dimensions K, BB and DD may be related by the equation:

$$K = \sqrt{DD^2 - BB^2}. \quad \text{EQ. 1}$$

Figure 24:
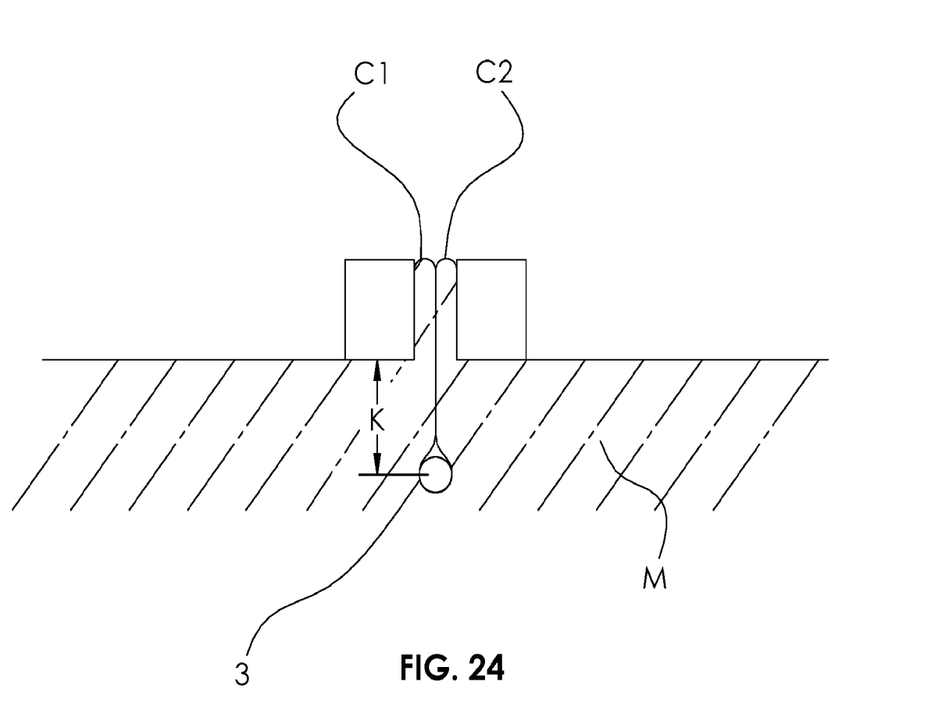
FIG. 24 depicts a front view of the fusing jaws in a closed position, with tissue to be fused disposed between the fusing jaws, and showing a preferred dimensional relationship between the depressor plunge depth and the closed fusing jaw opening.

Referring now to FIG. 24, a view of the fusing jaws in a closed position, with tissue to be fused disposed between the fusing jaws, is depicted. Tissue is depicted as M. C1 and C2 have been motivated together with the fusing jaws gripping the tissue originally located between C1 and C2, in FIG. 23, other than that tissue motivated away from the jaws by the depressor 3. Fusing energy may then be applied by the fusing elements as command by the user via a footswitch or other user control interface.

In the best mode of the invention, the value of K in EQ. 1 may be a number between 0% and 50% of the distance between C1 and C2. The preferred value of K is a number between 10% and 50% of the distance between C1 and C2. While these relationships are defined for the best mode, they are not limiting as to other embodiments of the invention, which may comprise any desired range for the value of K in relation to the distance between C1 and C2.

In any of the embodiments, depressor 3 is adapted to be retracted towards the fusing jaws in a direction predominantly perpendicular to a depressor longitudinal axis by the effect of guide pin 17 (see FIGS. 7 and 8).

In any of the embodiments, depressor 3 may comprise a malleable material.

Figure 25:
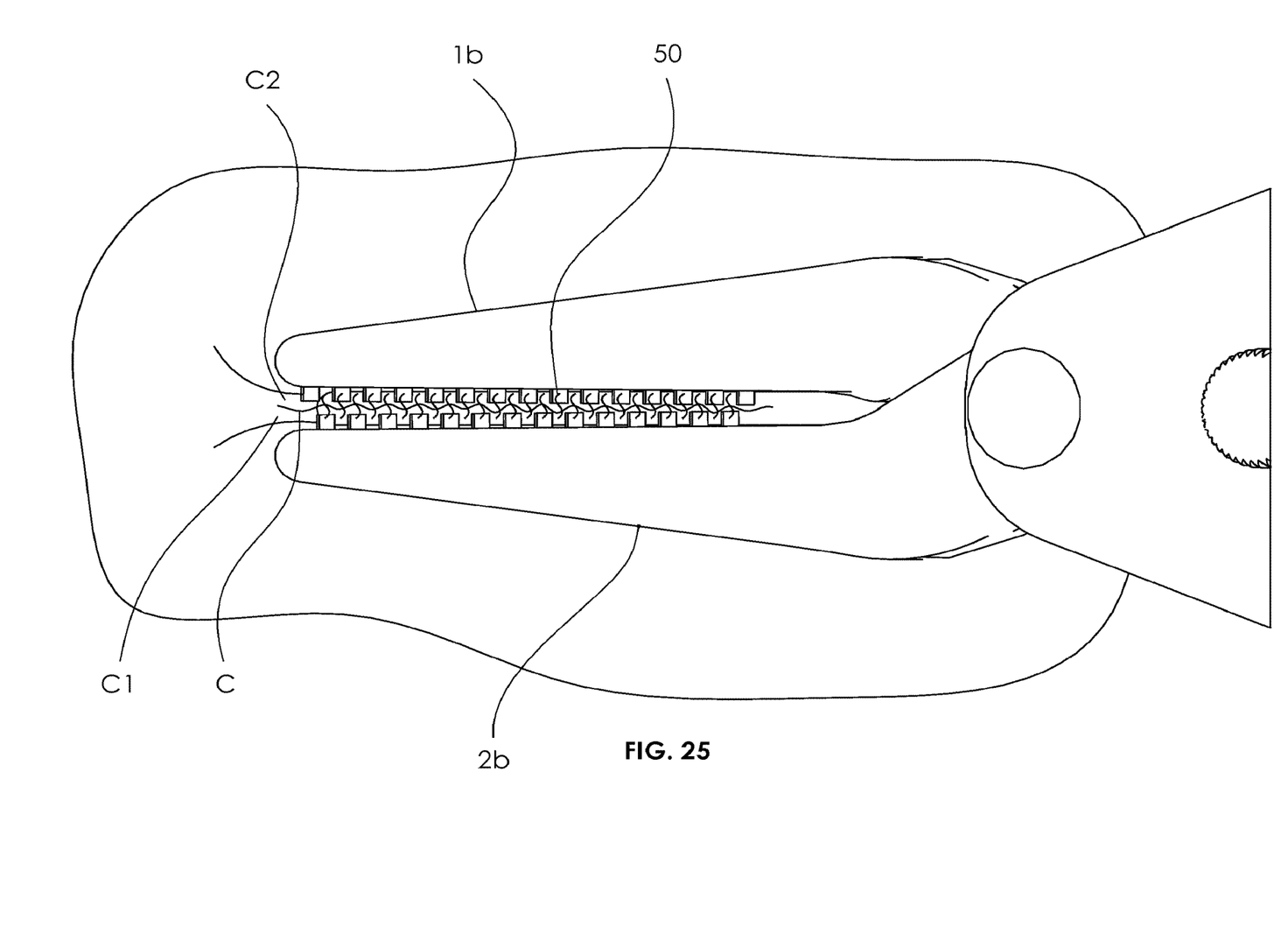
FIG. 25 depicts a top view of the fusing jaws in a closed position, with tissue to be fused disposed between the fusing jaws, showing an embodiment of the complimentary offset features that operate to stretch the tissue to be fused prior to and during fusing of the tissue.

Referring now to FIG. 25, a top view of the fusing jaws in a closed position, with tissue to be fused disposed between the fusing jaws 1b and 2b, showing an embodiment of the complimentary offset features that operate to stretch the tissue to be fused C1 and C2 prior to and during fusing of the tissue, is depicted. Fusing energy 50 is generated by the fusing elements of the invention when they are activated, causing the fusing of tissue C1 and tissue C2 to create a fused tissue bond C.

Figure 26:
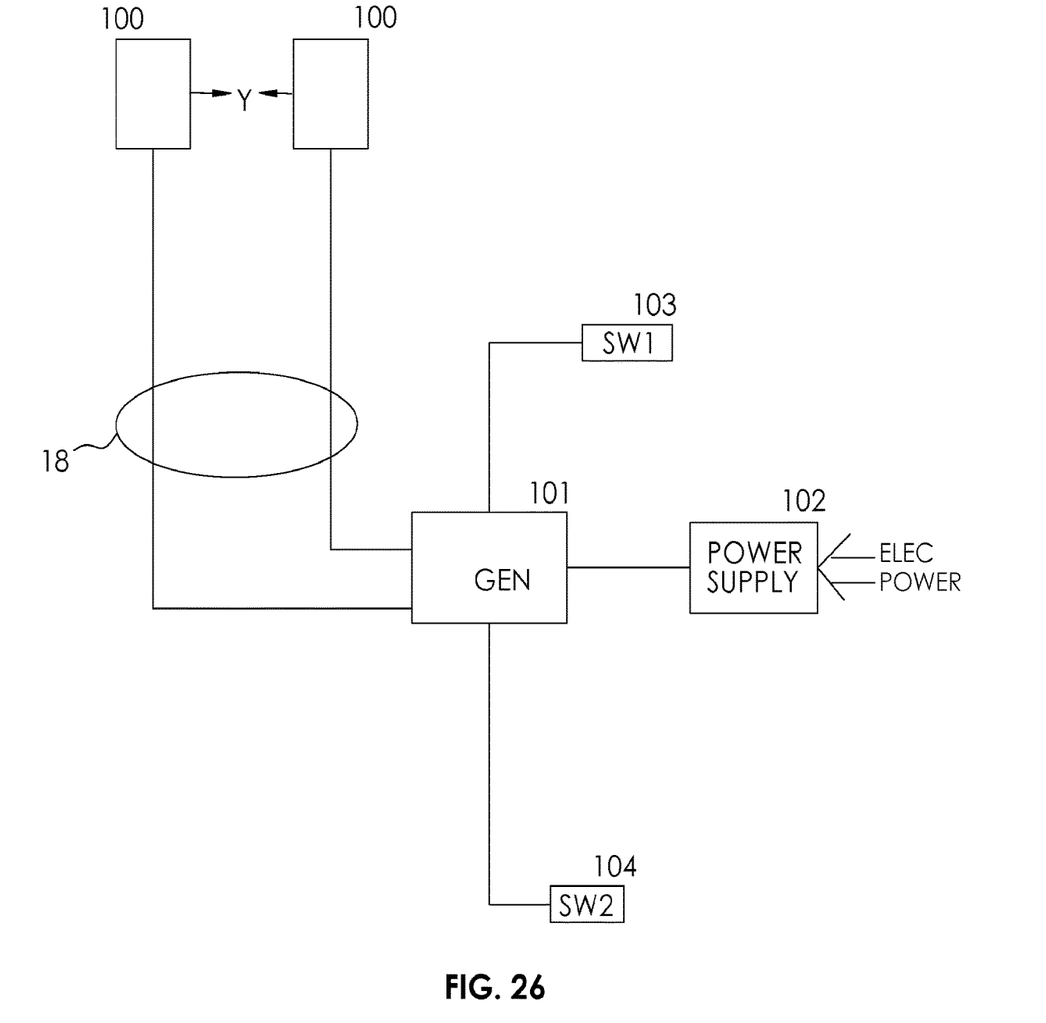
FIG. 26 depicts an electrical block diagram of the invention, depicting the fusing generator, fusing elements, foot switch for activating the fusing generator, and safety switch.

Referring now to FIG. 26, a block diagram of the electrical components of the system are depicted. The tissue fusing elements 100, which may be any fusing elements such as ultrasonic transducers or lasers and which are disposed in the fusing jaw so as to apply fusing energy Y for the fusing of tissue, are in electrical communication with a fusing generator 101 that provides a fusing signal, which may comprising fusing energy, to the fusing elements for the fusing of tissue. Fusing generator 101 may also be in electrical communication with a foot switch, or other switch, 104, which may be used by the user to activate and deactivate the signal from the generator to tissue fusing elements 100. Thus, for example, a surgeon is able to activate or deactivate the tissue fusing elements by operation of the foot pedal, leaving the surgeon's hands free. The tissue fusing clamp of the invention may further comprise a means 103, such as a switch, for disabling the tissue fusing elements 100 when the tissue fusing elements are separated by a maximum separation distance. The means 103 for disabling the tissue fusing elements 100 may be, for example, an electrical switch 103 in communication with the fusing generator 101 that senses when the components 1 and 2 are pivoted so as to be disposed at greater than a minimum opening angle that is related to the maximum safe fusing jaw opening dimension, which may be, for example, 10 mm.

The invention further comprises a method for the fusing of human or non-human biological tissue, comprising the steps of:

a. placing fusing jaws of a tissue using clamp on human or animal tissue to be fused, the fusing jaws being in an open session, wherein the fusing jaw comprise fusing elements;

b. disposing a depressor between the fusing jaws of the tissue clamp such that the pressure is in contact with an area of tissue between fusing jaws;

c. motivating the tissue fusing jaws together and causing the tissue fusing jaws to grasp the tissue to be fused while simultaneously motivating the depressor in a downward direction to a plunge depth such that it presses tissue downward in an area between the tissue to be fused, preventing such tissue from being pinched between the jaws, and pulling the tissue to be fused upwards such that it is disposed between the fusing jaws;

d. activating the fusing elements, causing fusing energy to be applied to the tissue to be fused and causing fusing of the tissue to be fused.

The fusing energy of the method may be any energy known to fuse biological tissue such as Radio Frequency (RF), ultrasonic or laser energy. The fusing energy may be bipolaor or unipolar.

The tissue to be fused for any embodiment of the apparatus or method of the invention may further be defined as human vaginal tissue.

In an embodiment, plunge depth K may be less than FW2.

The above described method and device may further comprise the limitation that the tissue fusing clamp opening is a minimum of twice the depressor plunge depth K, where the depressor plunge depth K is measured from the interior extent of a gripping feature disposed on an underneath surface of the tissue fusing jaws as depicted by dimension K in FIG. 21.

In a further alternate embodiment, the adjustability of plunge depth K may be eliminated by eliminating thumb screw 6 and slot 31. In this embodiment, link 10 may be attached to wedge 9 by any method known in the mechanical arts. The length of link 10 may be any predetermined length desired to achieve a specific plunge depth K.

In a further alternate embodiment, depressor 3 may fixed at a given predetermined distance K below the fusing jaws. In this embodiment, depressor 3 is static and may be affixed to an underneath surface of cover 4 or any other static structure, or any structure attached to cover 4. Thus, in this embodiment, depressor 3 is not motivated away from the fusing jaws when the fusing jaws are motivated towards a closed position. A variety of this embodiment of the invention may be produced, each embodiment having a different fixed distance K, for differing patients, tissue types, or surgeon preference.

While specific embodiments of mechanical features are shown in the figures and described herein, it is to be understood that the scope of the invention includes not only the mechanical features shown but equivalent structures as well, and that the features and elements of the invention may be present in any combination.

What is claimed is:

1. A tissue fusing clamp for fusing human or non-human biological tissue, comprising:

a first component and a second component pivotably attached to one another, wherein said first component comprises a first fusing jaw on a proximal end of said first component and wherein said second component comprises a second fusing jaw on a proximal end of said second component, said first and second fusing jaws for fusing tissue when said first and second fusing jaws are motivated together such that they grip tissue to be fused between them, forming a closed position;

a depressor attached to said first and second components and disposed between said first and second fusing jaws, said depressor adapted to be motivated in a direction away from said first and second fusing jaws when said first and second fusing jaws are motivated towards said closed position;

wherein said motivation of said depressor causes said depressor to press against tissue located between the tissue to be fused, moving said tissue located between the tissue to be fused away from said fusing jaws while said fusing jaws grip said tissue to be fused;

wherein said first and second fusing jaws comprise fusing elements capable of fusing tissue; and wherein said depressor is attached to said first and second components by a series of links attached to a wedge, said wedge slidingly engaged with an interior surface of each of said first and second components such that motivation of said first and second components towards the closed position motivates the wedge backwards and upwards, causing the wedge to motivate the links, and causing the depressor to be motivated.

2. The tissue fusing clamp of claim 1, wherein said first and second component each comprise a handle on a distal end such that motivation of the first and second component handles towards each other cause said first and second fusing jaws to be motivated towards the closed position.

3. The tissue fusing clamp of claim 2 wherein said first fusing jaw and said second fusing jaw grasp tissue to be fused on either side of said depressor when said first and second components are motivated into the closed position, bringing the tissue to be fused upwards and around said depressor while said depressor is being motivated away from said first and second fusing jaws such that the tissue to be fused is disposed between said first and second fusing jaws when said first and second fusing jaws are in the closed position.

4. The tissue fusing clamp of claim 1 wherein said first fusing jaw and said second fusing jaw grasp tissue to be fused on either side of said depressor when said first and second components are motivated into the closed position, bringing the tissue to be fused upwards and around said depressor while said depressor is being motivated away from said first and second fusing jaws such that the tissue to be fused is disposed between said first and second fusing jaws when said first and second fusing jaws are in the closed position.

5. The tissue fusing clamp of claim 1, further comprising a means for adjusting an opening dimension between said first and second fusing jaws when the tissue fusing clamp is in an open position.

6. The tissue fusing clamp of claim 1, wherein said fusing elements are selected from the group consisting of RF emitters or ultrasonic transducers.

7. The tissue fusing clamp of claim 1, wherein said fusing elements are lasers.

8. The tissue fusing clamp of claim 1, further comprising a means for disabling said tissue fusing elements when the tissue fusing elements are separated by a maximum separation distance.

9. The tissue fusing clamp of claim 1, wherein the tissue to be fused is further defined as tissue that is resting predominantly parallel to a long axis of the first and second fusing jaws and is disposed between said first and second fusing jaws.

10. The tissue fusing clamp of claim 1, comprising means for motivating the depressor towards the first and second fusing jaws at the same time that the first and second fusing jaws are motivated towards an open position.

* * * * *